(12) United States Patent
Scampini

(10) Patent No.: US 6,526,303 B1
(45) Date of Patent: Feb. 25, 2003

(54) DISPOSABLE DEFIBRILLATION AND EXTERNAL PACING ELECTRODE

(75) Inventor: Steven Anthony Scampini, Bedford, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 244 days.

(21) Appl. No.: 09/698,393

(22) Filed: Oct. 27, 2000

(51) Int. Cl.$^7$ ............................................. A61B 5/0408
(52) U.S. Cl. ..................... 600/391; 600/386; 607/153
(58) Field of Search .................... 607/153, 152, 607/115, 148; 600/386, 391, 394, 392, 397, 395

(56) References Cited

U.S. PATENT DOCUMENTS

| | | | | |
|---|---|---|---|---|
| 4,270,544 A | * | 6/1981 | Gilden et al. ............... | 600/392 |
| 4,441,501 A | * | 4/1984 | Parent ......................... | 600/381 |
| 4,444,194 A | * | 4/1984 | Burcham ..................... | 600/394 |
| 4,559,950 A | * | 12/1985 | Vaughan et al. ............ | 600/394 |
| 4,583,551 A | * | 4/1986 | Pike ............................ | 600/392 |
| 4,617,935 A | * | 10/1986 | Cartmell et al. ............ | 600/392 |

* cited by examiner

*Primary Examiner*—Willis R. Wolfe

(57) ABSTRACT

The present disclosure relates to a defibrillation/pacing electrode that comprises an electrode body, a conductor element, and an adhesive layer. When the electrode is in use, electrically conductive gel can be placed between the electrode and the patient's skin to form low impedance contact therebetween. In one embodiment, the electrically conductive gel is contained within a reservoir provided on the body, wherein the electrically conductive gel can be delivered from the reservoir to a patient's skin. In another embodiment, the electrically conductive gel is delivered to the skin through a valve mounted on the top surface of the body. In a further embodiment, the electrically conductive gel is supplied by a plurality of rupturable capsules that are impregnated within the adhesive layer.

25 Claims, 3 Drawing Sheets

DISPOSABLE DEFIBRILLATION AND EXTERNAL PACING ELECTRODE

FIELD OF THE INVENTION

The present disclosure relates to a disposable defibrillation/pacing electrode. More particularly, the present disclosure relates to an electrode with which low impedance connectivity can be achieved with the surface of the skin.

BACKGROUND OF THE INVENTION

Automatic external defibrillators normally include disposable electrodes that are used to deliver electrical shocks to a patient. Normally, these electrodes are applied to defibrillate the patient or to provide for external pacing of the patient's heart.

The electrodes typically comprise a plastic disc that includes a conductive layer that distributes the current transmitted to the electrode by the defibrillator. Conventionally, such electrodes further include a layer of adhesive material that is used to adhere the electrode to the patient's chest prior to and during delivery of the shocks. The adhesive material typically comprises a solid gel material that contains ionic compounds which increase the material's electrical conductivity to provide a low resistance path for current to flow to the patient's chest.

As known in the art, electrodes used with automatic external defibrillators often are stored for relatively long periods of time until needed. During this time, the adhesive material can become desiccated. This desiccation decreases the effectiveness of the material in that it lowers the material's conductivity, which in turn raises the impedance at the contact area between the electrode and the skin. This increased impedance results in less current reaching the patient's heart. Due to the problem of desiccation, the adhesive material normally is covered with a removable backing that reduces the material's exposure to air. Despite the provision of such backings, however, conventional adhesive materials still tend to dry out.

From the above, it can be appreciated that it would be desirable to have a disposable electrode that overcomes the effects of adhesive material desiccation to ensure low impedance contact between the electrode and skin.

SUMMARY OF THE INVENTION

The present disclosure relates to a defibrillation/pacing electrode that comprises an electrode body, a conductor element, and an adhesive layer. When the electrode is in use, electrically conductive gel can be placed between the electrode and the patient's skin to form low impedance contact therebetween. In one embodiment, the electrically conductive gel is contained within a reservoir provided on the body, wherein the electrically conductive gel can be delivered from the reservoir to a patient's skin. In another embodiment, the electrically conductive gel is delivered to the skin through a valve mounted on the top surface of the body. In a further embodiment, the electrically conductive gel is supplied by a plurality of rupturable capsules that are impregnated within the adhesive layer.

The features and advantages of the invention will become apparent upon reading the following specification, when taken in conjunction with the accompanying drawings.

BRIEF DESCRIPTION OF THE DRAWINGS

The invention can be better understood with reference to the following drawings. The components in the drawings are not necessarily to scale, emphasis instead being placed upon clearly illustrating the principles of the present invention.

DETAILED DESCRIPTION

Figure 1:
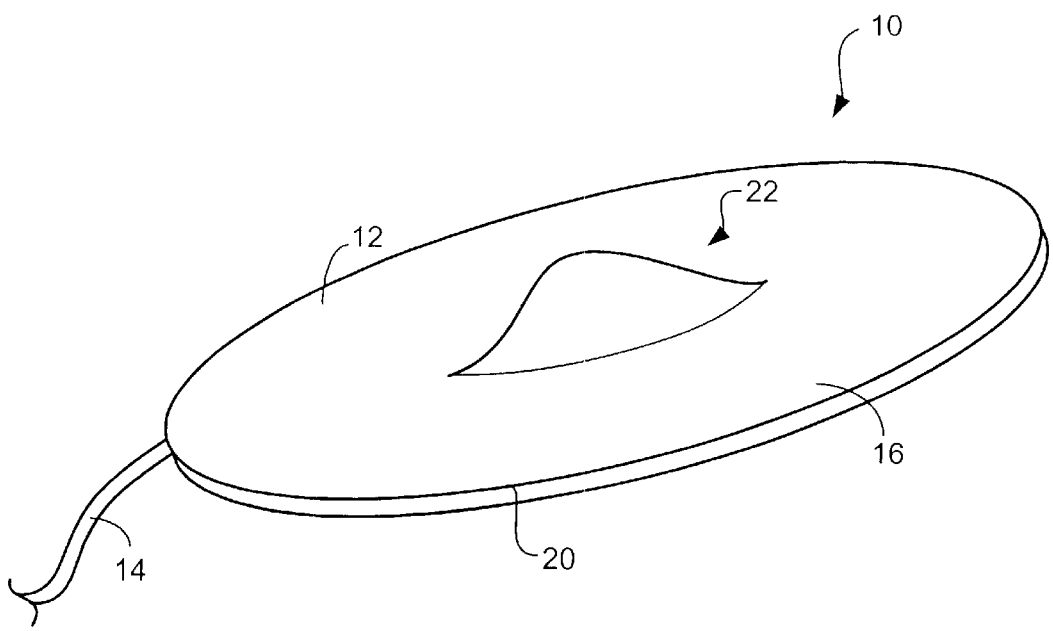
FIG. 1 is a perspective view of a first embodiment of a disposable electrode of the present invention.
Figure 2:
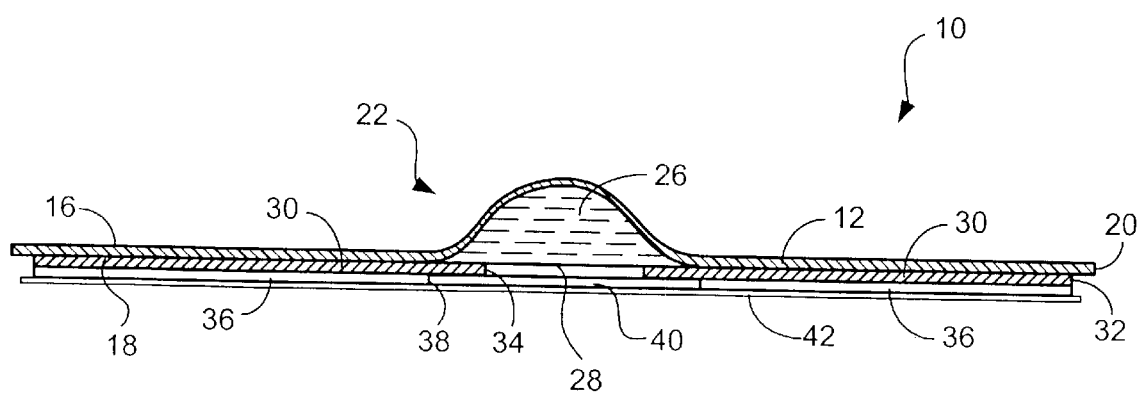
FIG. 2 is a cross-sectional view of the electrode shown in FIG. 1.

Referring now in more detail to the drawings, in which like numerals indicate corresponding parts throughout the several views, FIGS. 1 and 2 illustrate a first embodiment of a disposable electrode 10 of the present invention. As indicated in FIG. 1, the electrode 10 generally comprises an electrode body 12 and an interconnect cord 14. The electrode body 12 comprises a top surface 16, a bottom surface 18, and an outer periphery 20. The outer periphery 20 can be shaped such that the electrode body 12 is generally elliptical. It is to be understood, however, that alternative shapes can be used.

As indicated in FIG. 2, the electrode body 12 is normally planar and relatively thin. The body 12 typically is normally constructed of a flexible material, such as a polymeric material, so that it can easily conform to the chest of the patient. Located in the center of the electrode body 12 is a reservoir 22. This reservoir 22 typically takes the form of a protuberance which extends upwardly from the top surface 16 of the electrode body 12. The reservoir 22 can be formed contiguously with the electrode body 12 to form a unitary component. Alternatively, the reservoir 22 can be formed separately from the electrode body 12, and attached subsequently to the formation of the body 12 to create an integral component. Regardless, the reservoir 22 is very pliable such that it can be easily deformed by the attending technician. By way of example, the reservoir 22 can be formed of a resilient yet substantially impermeable material such as a rubber material.

Disposed within the reservoir 22 is a bolus of electrolytic gel 26. The gel 26 normally comprises a highly viscous liquid that contains a high concentration of ionic compounds that renders the gel electrically conductive. The gel 26 is encapsulated within the reservoir 22 with a rupturable member 28 that is connected to the bottom surface 18 of the electrode 12. Preferably, this member 28, as well as the reservoir, is constructed of a substantially impermeable material to prevent the gel 26 from drying out. The member 28 is normally very thin such that it can be easily ruptured in response to the reservoir 22 being pressed and squeezed to permit the gel 26 to flow from the reservoir 22 to the patient's skin. As indicated in FIG. 2, the gel mass is stored in a substantially spherical orientation to reduce its surface area to further reduce its susceptibility to desiccation. Notably, the gel 26 is segregated from the conductor element (described below) when encapsulated within the reservoir 22. This configuration is desirable in that the ionic compounds contained within the gel 26 can be highly corrosive to the conductor element. Indeed, because the gel 26 is segregated from the conductor element, the gel can be optimized for electrical conductivity without regard to its corrosiveness. Accordingly, highly corrosive ionic compounds can be used, if desired. In addition or instead, an easily corrodible material can be used for construction of the conductor element to lower the cost of the electrode 10.

Connected to the bottom surface 18 of the electrode body 12 is a conductor element 30. The conductor element 30 is formed of an electrically conductive material such as a metal material. Normally, the conductor element 30 is similar in size and shape to the electrode body 12, although it typically is slightly smaller such that its outer periphery 32 is formed inside of the outer periphery 20 of the body 12. In a preferred arrangement, the conductor element 30 is constructed of an inexpensive material to reduce manufacturing costs of the electrode 10. By way of example, the conductor element 30 can comprise a foil material or a thin metalized layer which is formed directly on the bottom surface 18 of the electrode body 12. In any case, the conductor element 30 is thin enough to ensure that the electrode 10 is sufficiently conformable. As indicated in FIG. 2, the conductor element 30 includes a central opening 34 which generally coincides with the reservoir 22. Preferably however, the central opening 34 is smaller in extent than the reservoir 22 to ensure positive contact between the element 30 and the gel 26. As is discussed below, this opening 34 also facilitates the administration of the electrolytic gel 26 to the patient's skin.

Contacting the conductor element 30 is an adhesive layer 36. This adhesive layer 36 preferably, although not necessarily, is composed of a solid, electrolytic gel that is also electrically conductive. Typically, the adhesive layer 36 extends to the outer periphery 32 of the conductor element 30. Similar to the conductor element 30, the adhesive layer 36 is provided with a central opening 38. As indicated in FIG. 2, this opening 38 is normally larger than the central opening 34 so as to form a gap 40 that can be filled with gel 26 once the member 28 has been ruptured. Covering the adhesive layer 36 prior to use of the electrode 10 is a removable backing 42 of conventional design. The backing 42 typically comprises an inner non-stick surface which enables the technician to easily remove it from the adhesive layer 36.

The general construction of the disposable electrode 10 having been described above, operation and use of the electrode 10 will now be discussed. Once it has been determined that a patient needs to be defibrillated or that the patient's heart must be externally paced, the attending technician can remove the backing 42 that covers the adhesive layer 36 by simply peeling it off. After the backing 42 has been removed, the disposable electrode 10 can be placed upon the patient's chest in the appropriate location. Due to the adhesive nature of the layer 36, the electrode 10 can be temporarily affixed in position by pressing the electrode 10 downwardly against the patient's chest.

Once the electrode 10 has been adhered to the patient's chest, the reservoir 22 can be pressed and/or squeezed to cause the member 28 to rupture. Upon rupturing, the member 28 permits the electrolytic gel 26 to flow into the gap 40 that is created by the conductor element 30 and the adhesive layer 36. When the gel 26 fills this gap 40, it comes into direct contact with the skin. Notably, in that the gel 26 is in liquid form, positive contact is made with the skin even where the patient is excessively hairy. Due to the relative sizes of the central openings 34 and 38 of the conductor element 30 and the adhesive layer 36, respectively, the gel 26 also makes positive contact with the conductor element 30 such that current supplied to the conductor element 30 will flow unimpeded to the gel 26, and therefore to the patient's chest. The provision of the gel 26 therefore ensures a low impedance contact between the electrode 10 and the patient's skin to ensure that the proper amount of current reaches the patient's heart.

Figure 3:
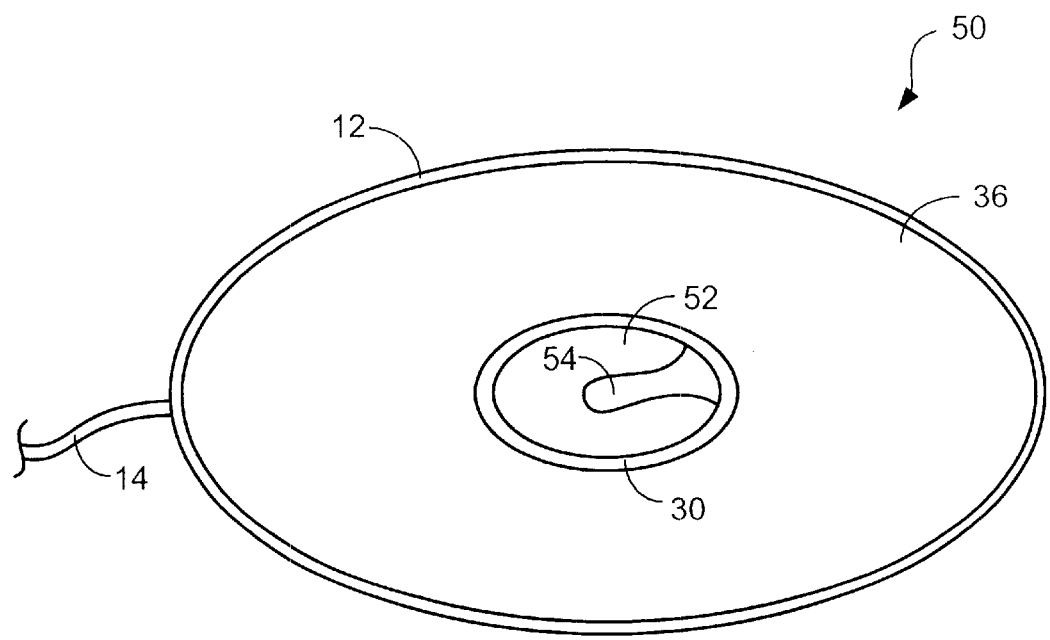
FIG. 3 is a bottom plan view of a second embodiment of a disposable electrode of the present invention.

FIG. 3 illustrates a second embodiment of a disposable electrode 50 of the present invention. This electrode 50 is substantially identical in construction to the electrode 10 shown in FIGS. 1 and 2. Accordingly, a detailed description of the construction of the electrode 50 will not be provided. It suffices to say that the electrode 50 includes a body 12, an interconnect cord 14, a conductor element 30, and an adhesive layer 36 just as in the first embodiment. However, instead of the rupturable member 28 shown in FIG. 2, the disposable electrode 50 includes a removable member 52 that encapsulates the gel within the reservoir (not visible in FIG. 3). As with the rupturable member 28, the removable member 52 preferably is made of a substantially impermeable material. As indicated in FIG. 3, the removable member 52 can be provided with a pull tab 54 with which the attending technician can remove the member 52 prior to applying the electrode 50 to the patient's skin. In use, the member 52 is removed and the electrode 50 is applied to the chest in the same manner as described above. Once the electrode is placed in the correct position, the reservoir is pressed and/or squeezed to make positive contact with the conductor element 30 and the patient's skin.

Figure 4:
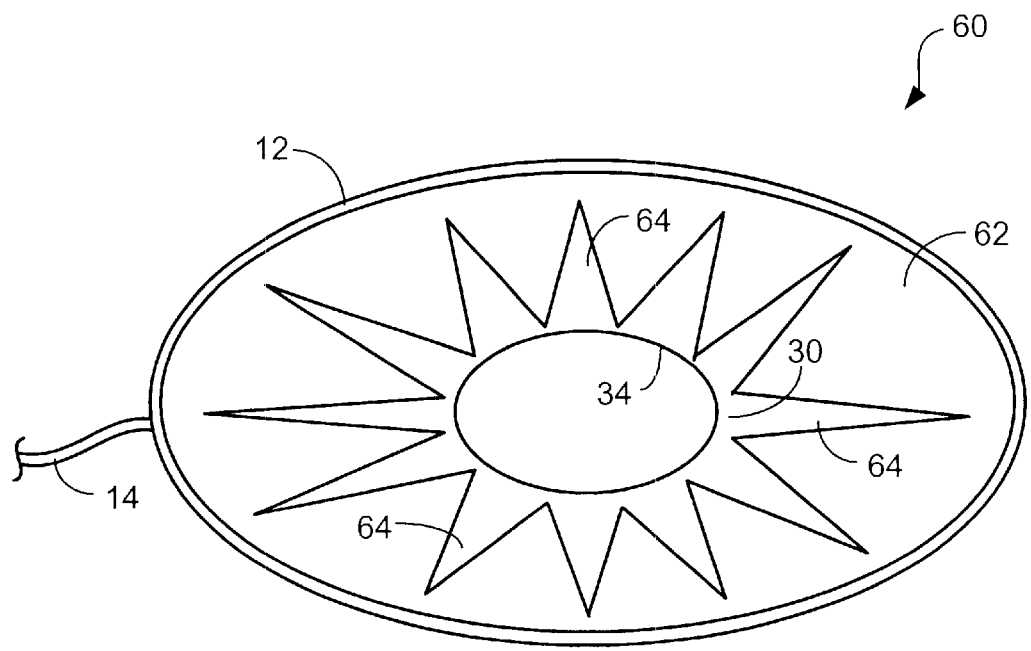
FIG. 4 is a bottom plan view of a third embodiment of a disposable electrode of the present invention.

FIG. 4 illustrates a third embodiment of a disposable electrode 60 of the present invention. Like the first and second embodiments, the disposable electrode 60 generally includes a body 12 and an interconnect cord 14. Furthermore, the electrode 60 is provided with a conductor element 30 and an adhesive layer 62. However, in the embodiment shown in FIG. 4, the adhesive layer 62 is formed in a pattern that includes a plurality of outwardly extending voids or channels 64. Normally, these voids 64 extend radially outward from the central opening 34 of the conductor element 30. With this configuration, gel from the reservoir 22 (not visible) can be urged into contact with the patient's skin not only in a central area of the electrode 60, but also towards the periphery of the electrode 60. With such an arrangement, a relatively large area of low impedance contact can be ensured regardless of the condition of the adhesive layer 62. Although a generally star-shaped pattern is illustrated in FIG. 4, it is to be understood that substantially any pattern providing radially extending voids, channels, or passageways could be used.

Figure 5:
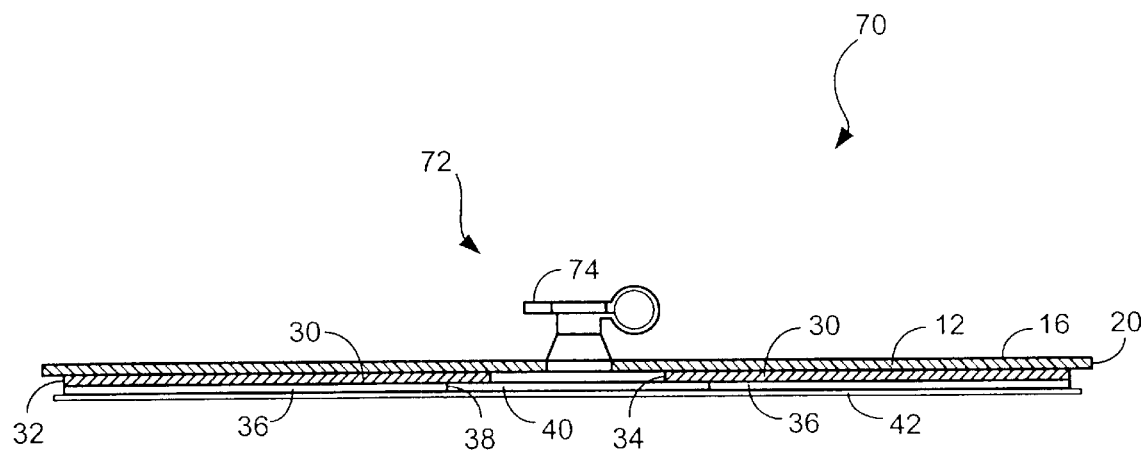
FIG. 5 is a cross-sectional view of a fourth embodiment of a disposable electrode of the present invention.

FIG. 5 illustrates a fourth embodiment of a disposable electrode 70 of the present invention. As with the disposable electrode 10 shown in FIGS. 1 and 2, the disposable electrode 70 includes an electrode body 12, and conductor element 30, and an adhesive layer 36 which can be covered with a removable backing 42. However, in the embodiment shown in FIG. 5, a valve 72 is provided on the electrode body 12. As indicated in this figure, this valve 72 can be formed unitarily with the electrode body 12 or, alternatively, can be formed separately and attached to the body 12 at a subsequent time to form an integral component. In a preferred arrangement, the valve 72 is inexpensive in design to keep the manufacturing costs of the electrode 70 low. By way of example, the valve 72 can comprise a flexible polymeric valve similar to those used in the construction of inflatable toys. In such an arrangement, the valve 72 includes a closure member 74 with which the valve can be opened and closed. Once opened, the valve 72 can be used to deliver liquid electrolytic gel from a separate reservoir, to the gap 40 of the disposable electrode 70 to provide for low impedance contact between the electrode 70 and the patient's skin. By way of example, the gel can be provided from a reservoir formed as a plastic tube, similar to a toothpaste tube or a Ketchup container (not shown) that can be stored along with the defibrillator. In such an embodiment, fresh electrolytic gel can always be made available.

Figure 6:
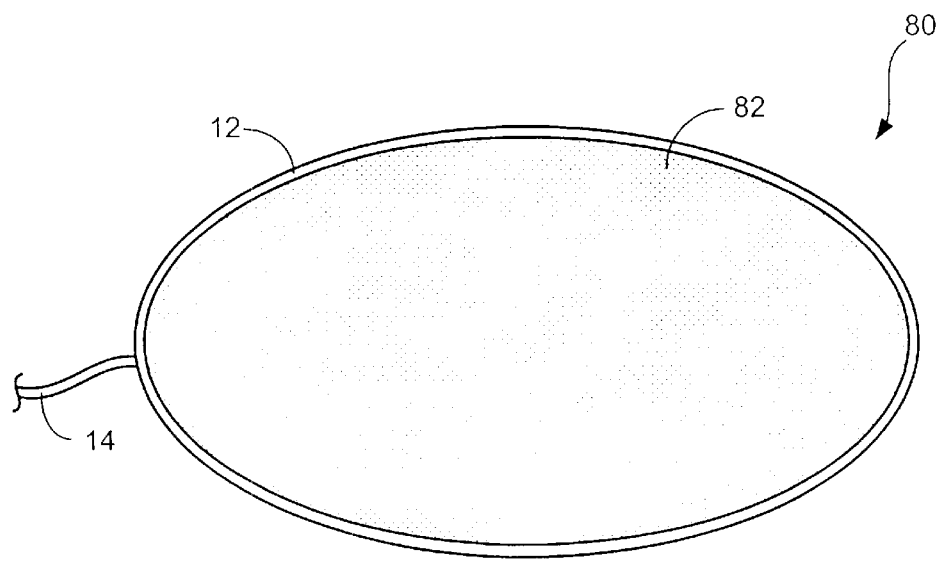
FIG. 6 is a bottom plan view of a fifth embodiment of a disposable electrode of the present invention.

FIG. 6 illustrates a fifth embodiment of a disposable electrode 80 of the present invention. As with the first disposable electrode 10, this electrode 80 includes an electrode body 12 and an interconnect cord 14. However, unlike the embodiment shown in FIGS. 1 and 2, the disposable electrode 80 does not comprise a reservoir for electrolyte gel. Because of this fact, the conductor element (not visible) and an adhesive layer 82 do not include central openings. Instead, the adhesive layer 82 is impregnated with a plurality of small, rupturable capsules (indicated with small dots) that contain a liquid electrolytic gel. By way of example, these members can comprise microspheres having thin polymer outer shells. Prior to use, the disposable electrode 80 can be kneaded (with backing in place) to rupture the members such that the liquid gel is released throughout the entirety of the adhesive layer 82. Alternatively, the members could be ruptured during the process of affixing one disposable electrode 80 to a patient by simply pressing on the electrode body 12. With this release of gel, a low impedance contact can be formed within the skin along the entire surface of the adhesive layer 82. Accordingly, if the adhesive layer 82 is electrically conductive, it can be rehydrated in this manner to "recharge" its electrical conductivity.

While particular embodiments of the invention have been disclosed in detail in the foregoing description and drawings for purposes of example, it will be understood by those skilled in the art that variations and modifications thereof can be made without departing from the scope of the invention as set forth in the following claims. For instance, although specific, separate embodiments have been illustrated and described, it is to be appreciated that the features of the various embodiments can be combined to form alternative variants that are equally effective in forming low impedance contact. In addition, it will be understood that, although the electrode is described as being used for defibrillation and pacing, the concepts disclosed herein can be applied to any medical electrode.

What is claimed is:

1. An electrode, comprising:
   an electrode body;
   a conductor element supported by the electrode body; and
   a reservoir storing an electrically conductive gel, the reservoir being in communication with the electrode body and being adapted to expel the electrically conductive gel so that the electrically conductive gel communicates with the conductor element,
   wherein the electrically conductive gel is encapsulated within the reservoir with a removable member.

2. An electrode comprising:
   an electrode body;
   a conductor element supported by the electrode body;
   a reservoir storing an electrically conductive gel, the reservoir being in communication with the electrode body and being adapted to expel the electrically conductive gel so that the electrically conductive gel communicates with the conductor element; and
   a valve connected to the electrode body that facilitates communication between the electrically conductive gel and the conductor element.

3. A method of using an electrode to form low impedance contact between the electrode and a patient's skin, comprising:
   placing an electrode on the patient, and
   supplying electrically conductive gel through the electrode so that the gel is in communication with both a conductor element of the electrode and the patient's skin,
   wherein the electrically conductive gel is supplied from a reservoir, formed as a protuberance that extends upwardly from a top surface of the electrode, that is filled with electrically conductive gel.

4. A method of using an electrode to form low impedance contact between the electrode and a patient's skin, comprising:
   placing an electrode on the patient; and
   supplying electrically conductive gel through the electrode so that the gel is in communication with both a conductor element of the electrode and the patient's skin,
   wherein the electrically conductive gel is supplied through a valve formed in the electrode that receives electrically conductive gel from a separate container.

5. A method of using an electrode to form low impedance contact between the electrode and a patient's skin, comprising:
   placing an electrode on the patient; and
   supplying electrically conductive gel through the electrode so that the gel is in communication with both a conductor element of the electrode and the patient's skin,
   wherein the electrically conductive gel is supplied by a plurality of capsules of electrically conductive gel that arc impregnated in an adhesive layer of the electrode.

6. An electrode, comprising:
   an electrode body;
   a conductor element supported by the electrode body;
   a reservoir storing an electrically conductive gel, the reservoir being in communication with the electrode body and being adapted to expel the electrically conductive gel so that the electrically conductive gel communicates with the conductor element, wherein the conductor element includes an opening that substantially coincides with the location of the reservoir, and
   an adhesive layer, attached to the conductor element, the adhesive layer including an opening that substantially coincides with the location of the reservoir and the opening of the conductor element to form a gap that can be filled with the electrically conductive gel,
   wherein the adhesive layer includes a plurality of voids that can be filled with the electrically conductive gel.

7. The electrode of claim 6, wherein the voids extend outwardly from generally the center of the electrode.

8. A defibrillation/pacing electrode, comprising:
   an electrode body;
   a conductor element attached to the body; and
   an adhesive layer in contact with the conductor element, the adhesive layer being impregnated with a plurality of rupturable capsules of electrically conductive gel.

9. The electrode of claim 8, wherein the capsules are microspheres of electrically conductive gel.

10. The electrode of claim 8, wherein the capsules comprise thin polymeric outer shells.

11. An electrode, comprising:
    an electrode body;
    a conductor element supported by the electrode body; and
    a reservoir storing an electrically conductive gel, the reservoir being in communication with the electrode body and being adapted to expel the electrically conductive gel so that tip electrically conductive gel communicates with the conductor element, wherein the reservoir is formed as a protuberance that extends upwardly from a top surface of the electrode body.

12. The electrode of claim 11, wherein the reservoir is made of a pliable material such that the reservoir can be easily deformed.

13. The electrode of claim 11, wherein the reservoir is located generally in the center of the electrode body.

14. The electrode of claim 11, wherein the electrically conductive gel is encapsulated within the reservoir with a rupturable member.

15. The electrode of claim 11, wherein the conductor element includes an opening that substantially coincides with the location of the reservoir.

16. The electrode of claim 15, further comprising an adhesive layer attached to the conductor element, the adhesive layer including an opening that substantially coincides with the location of the reservoir and the opening of the conductor element to form a gap that can be filled with the electrically conductive gel.

17. The electrode of claim 16, wherein the adhesive layer is formed of a solid gel that contains ionic compounds.

18. A defibrillation/pacing electrode, comprising:
    an electrode body having a top surface;
    a conductor element attached to the body;
    an adhesive layer in contact with the conductor element; and
    a valve mounted on the top surface of the body through which electrically conductive gel can be delivered to a patient's skin.

19. The electrode of claim 18, wherein the valve is located generally in the center of the body.

20. The electrode of claim 18, wherein the adhesive layer is formed of a solid gel that contains ionic compounds.

21. The electrode of claim 18, in combination with a separate container for holding the electrically conductive gel.

22. The electrode of claim 18, wherein the conductor element includes an opening that substantially coincides with the location of the valve.

23. The electrode of claim 22, wherein the adhesive layer includes an opening that substantially coincides with the location of the reservoir and the opening of the conductor element to form a gap that can be filled with the electrically conductive gel.

24. The electrode of claim 18, wherein the adhesive layer includes a plurality of voids that can be filled with the electrically conductive gel.

25. The electrode of claim 24, wherein the voids extend outwardly from generally the center of the electrode.

* * * * *